(12) United States Patent
Mainguet et al.

(10) Patent No.: US 10,176,357 B2
(45) Date of Patent: Jan. 8, 2019

(54) FINGERPRINT OR PALMPRINT SENSOR

(71) Applicants: Commissariat à l'Energie Atomique et aux Energies Alternatives, Paris (FR); SAFRAN IDENTITY & SECURITY, Issy-les-Moulineaux (FR)

(72) Inventors: Jean-François Mainguet, Grenoble (FR); Joel Yann Fourre, Marly-le-Roi (FR); Josep Segura Puchades, Fontaine (FR)

(73) Assignees: COMMISSARIAT À L'ENERGIE ATOMIQUE ET AUX ENERGIES, Paris (FR); SAFRAN IDENTITY & SECURITY, Issy-les-Moulineau (FR)

( * ) Notice: Subject to any disclaimer, the term of this patent is extended or adjusted under 35 U.S.C. 154(b) by 16 days.

(21) Appl. No.: 15/516,402

(22) PCT Filed: Sep. 30, 2015

(86) PCT No.: PCT/FR2015/052616
§ 371 (c)(1),
(2) Date: Apr. 1, 2017

(87) PCT Pub. No.: WO2016/051087
PCT Pub. Date: Apr. 7, 2016

(65) Prior Publication Data
US 2017/0293791 A1     Oct. 12, 2017

(30) Foreign Application Priority Data
Oct. 3, 2014 (FR) ..................... 14 59494

(51) Int. Cl.
G06K 9/28     (2006.01)
G06K 9/00     (2006.01)
(Continued)

(52) U.S. Cl.
CPC ........ *G06K 9/00013* (2013.01); *A61B 5/1172* (2013.01); *G06K 9/0002* (2013.01);
(Continued)

(58) Field of Classification Search
CPC .................................... G06K 9/00006–9/0012
See application file for complete search history.

(56) References Cited

U.S. PATENT DOCUMENTS

2014/0354597 A1* 12/2014 Kitchens, II .......... G06F 1/3215
345/175

FOREIGN PATENT DOCUMENTS

EP      0977275 A1     2/2000
JP      2006343229 A   12/2006
(Continued)

OTHER PUBLICATIONS

PCT International Search Report; International Application No. PCT/FR2015/052616; dated Jan. 4, 2016, 3 pages.
(Continued)

*Primary Examiner* — Brian Werner
(74) *Attorney, Agent, or Firm* — Moreno Intellectual Property Law LLC

(57) ABSTRACT

The invention relates to a print sensor (160) comprising, on a transparent support substrate, a plurality of elementary acquisition cells (161), each cell comprising a photodetector (PS), a pyroelectric conversion element (PYR), and at least one TFT transistor (RT, SF) connected to both the photodetector (PS) and the pyroelectric conversion element (PYR).

12 Claims, 3 Drawing Sheets

(51) Int. Cl.
*H04N 5/3745* (2011.01)
*A61B 5/1172* (2016.01)

(52) U.S. Cl.
CPC ......... *G06K 9/0004* (2013.01); *G06K 9/0012* (2013.01); *G06K 9/00053* (2013.01); *G06K 9/00087* (2013.01); *H04N 5/3745* (2013.01)

(56) References Cited

FOREIGN PATENT DOCUMENTS

WO 2012/0158950 A1 11/2012
WO 2014/091093 A1 6/2014

OTHER PUBLICATIONS

Maltoni, Davide et al.; Chapter 2: Fingerprint Sensing; Handbook of Fingerprint Recognition; p. 57-95; Jan. 1, 2009.
Mainguet, Jean-François; Biometrics: Fingerprint sensing techniques; from http://web.archive.org; Sep. 27, 2014.
Han, Hiro; Characteristics of Thermal-type Fingerprint Sensor; Proceedings of SPIE; vol. 6944; Mar. 16, 2008.
Written Opinion of the International Searching Authority; International Application No. PCT/FR2015/052616; 9 pages.

* cited by examiner

FINGERPRINT OR PALMPRINT SENSOR

The present patent application claims the priority benefit of French patent application FR14/59494 which will be incorporated herein by reference.

BACKGROUND

The present disclosure relates to the field of fingerprint or palmprint sensors.

DISCUSSION OF THE RELATED ART

Various types of sensors have been provided to perform an electronic acquisition of a fingerprint and/or a palmprint, that is, to provide an image of the pattern formed by the ridges and valleys of the skin of a finger, of a plurality of fingers, and/or of the palm of the hand. Optical sensors, capacitive sensors, thermal sensors, ultrasound sensors, and electric field sensors have in particular been provided.

Print sensors designed in TFT ("Thin Film Transistor") technology, that is, comprising, on a support substrate, one or a plurality of elementary acquisition cells, each elementary cell (or pixel) comprising an acquisition element, for example, photoelectric, pyroelectric, or capacitive, and one or a plurality of TFTs enabling to control this element, are here more particularly considered. TFT here means transistors formed by successive depositions of conductive, insulating, and semiconductor layers on the support substrate. In particular, in a TFT, the semiconductor channel-forming region of the transistor is formed by deposition of a layer of a semiconductor material, for example, hydrogenated amorphous silicon, polysilicon (silicon which is made polycrystalline after an anneal, for example), or also a material of IGZO ("Indium Gallium Zinc Oxide") type, where such a deposition may be preceded by the deposition of a conductive layer used to form a gate, source, or drain electrode of the transistor. Print sensors made in TFT technology have the advantage of having a relatively low cost, particularly due to the use of a support substrate made of a low-cost material such as glass (instead of a single-crystal silicon substrate generally used to form transistors) and of being easily integratable in many types of electronic devices, and in particular in devices already using the TFT technology to carry out other functions, for example, to form display screens. The TFT technology is particularly advantageous in the field of print sensors where the sensor surface is substantially identical to the surface of the print to be acquired, that is, where no optical focusing system (or lens) is placed between the sensor and the object of which an image is desired to be acquired. Indeed, due to their large sizes, the forming of such sensors inside and on top of the silicon substrates would have much too high a cost for most applications.

SUMMARY

An embodiment provides a fingerprint or palmprint sensor comprising: on a support substrate, a plurality of elementary acquisition cells, each cell comprising a photodetector, a pyroelectric conversion element, and at least one TFT; an illumination light source; and a heat source distinct from the light source.

According to an embodiment, the support substrate is transparent.

According to an embodiment, the photodetector and the pyroelectric conversion element are connected in parallel.

According to an embodiment, the sensor comprises a circuit capable of controlling the acquisition of a thermal image and the acquisition of an optical image by the sensor cells, the circuit being capable, during the entire optical image acquisition phase, of turning on the light source and of keeping the heat source off and, during the entire thermal image acquisition phase, of keeping the light source off.

According to an embodiment, the sensor comprises a circuit capable of controlling the acquisition of a thermal image and the acquisition of an optical image by the sensor cells, the circuit being capable of implementing the acquisition of the thermal image during part of an integration period of the optical image acquisition phase during which the light source is on.

According to an embodiment, in each cell, the photodetector and the pyroelectric conversion element are connected to a capacitive node of the cell.

According to an embodiment, in each cell, the photodetector and the pyroelectric conversion element are connected to an intermediate node of the cell, the intermediate node being coupled to a capacitive sense node of the cell by a selection transistor, and each cell further comprising: a reference capacitor connected between the capacitive sense node and a node of application of a control signal; and an electrode connected to the capacitive sense node, the electrode being coated with a dielectric layer and being intended to form a capacitance with a user's skin for a capacitive acquisition of a print image.

According to an embodiment, the photodetector and the pyroelectric conversion element are connected to a same selection transistor enabling, in the off state, to isolate the photodetector from the pyroelectric element.

According to an embodiment, the cells are arranged in an array of rows and columns, and the heat source is controllable to heat the cells row by row.

According to an embodiment, the cells are voltage readout cells, each cell comprising: a capacitive sense node having the photodetector and the pyroelectric conversion element coupled thereto; a reset transistor coupling the capacitive sense node to a node of application of a reset potential; and a readout circuit comprising a transistor assembled as a follower source, having its gate connected to the sense node, and having its source coupled to an output track of the cell via a readout transistor.

According to an embodiment, the cells are charge readout cells, each cell comprising: a capacitive sense node having the photodetector and the pyroelectric conversion element coupled thereto; and a readout transistor coupling the sense node to an output track of the cell.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION OF THE PRESENT EMBODIMENTS

Figure 1:
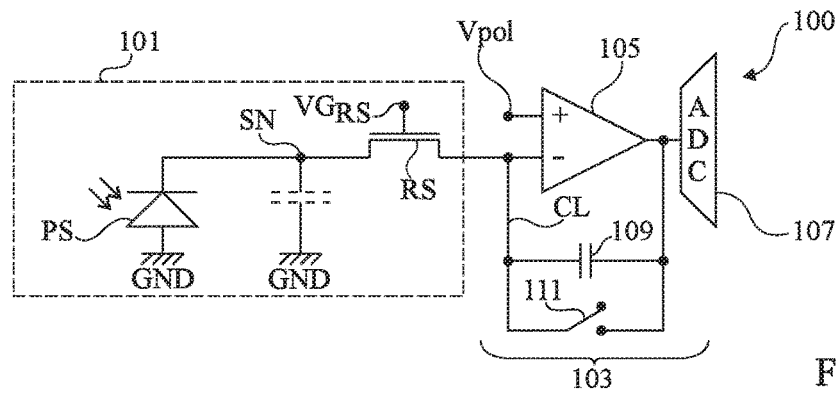
FIG. 1 is a partial electric diagram illustrating an example of an optical TFT print sensor.

For clarity, the same elements have been designated with the same reference numerals in the different drawings. Further, only those elements which are useful to the understanding of the described embodiments have been detailed. In particular, the peripheral control circuits of the elementary cells of the described TFT print sensors have not been detailed, the forming of such circuits being within the abilities of those skilled in the art on reading of the present description. It should further be noted that in the present description, when architectures of elementary cells, of elementary cell arrays, or of print sensors are described, term "connected" is used to designate a direct electric connection, with no intermediate electronic component, for example, by means of a conductive track, and term "coupled" is used to designate an electronic connection which may be direct or via intermediate components, for example, via a transistor.

FIG. 1 is an electric diagram illustrating an example of an optical TFT print sensor 100. Sensor 100 comprises a plurality of identical or similar elementary acquisition cells 101, made in TFT technology on a surface of a transparent support substrate, for example, made of glass, which will be called hereafter, by convention, the upper surface of the substrate. For simplification, a single cell 101 has been shown in FIG. 1. Each cell 101 comprises a photodetector PS, for example, a photodiode having its anode coupled to a node of application of a reference potential GND (for example, the ground), and having its cathode connected to a capacitive sense node SN of the cell. As an example, photodetector PS is a PIN-type photodiode, or an organic photodiode. In FIG. 1, the capacitance of sense node SN has been shown in dotted lines in the form of a capacitor having an electrode connected to node SN and having its other electrode connected to node GND. In practice, the capacitance of node SN may be a stray capacitance of another element of the cell, for example, the stray capacitance of photodiode PS (to which the stray capacitance of transistor RS is added in the shown example) or a specific capacitance. For simplification, the capacitance of node SN will not be shown in the following drawings. Each cell 101 further comprises a readout transistor RS coupling its sense node SN to an output conductive track CL of the cell. The control gate of transistor RS is connected to a node $VG_{RS}$ of application of a control potential of the transistor. Output track CL of cell 101 is connected to an output stage 103 of the sensor. In this example, output stage 103 comprises an operational amplifier 105 having an inverting input (−) coupled to track CL and having a non-inverting input (+) coupled to a node $V_{pol}$ of application of a bias potential. Output stage 103 further comprises an analog-to-digital converter 107 (ADC) having its input coupled to the output of amplifier 105. In the shown example, the output stage further comprises a capacitor 109 in parallel with a control switch 111 between the inverting input (−) and the output of amplifier 105.

Sensor 100 further comprises an illumination light source, not shown. As an example, the illumination source is arranged on the side of the substrate surface opposite to cells 101, which will be called hereafter by convention the lower surface of the substrate.

Sensor 100 operates as follows: The user places one (or a plurality of) finger(s) on or above the upper surface of the sensor (on the side of cells 101). The backlighting light source, arranged on the substrate side opposite to the cells, illuminates the finger through transparent areas of the assembly formed by the support substrate and cells 101. The light is then backscattered by the finger towards photodiodes PS with, at the level of each cell 101, a variable attenuation according to whether the finger portion located above the cell corresponds to a ridge or to a valley of the finger skin. As a variation, the light source may be placed above or next to the finger, the light being then transmitted by the finger towards photodiodes PS of the sensor, with a variable attenuation according to whether the finger portion located above the cell corresponds to a ridge or to a valley of the finger skin. In this case, the substrate may be non-transparent. During an integration period of a cell 101, the readout transistor RS of the cell is non-conductive, and the light reflected by the finger is converted into electric charges by photodiode PS of the cell. The charges are stored on sense node SN of the cell. At the end of the integration period, the photogenerated charges are transferred onto output track CL of the cell (which may have been previously reset by turning-on of switch 111) via transistor RS, and the resulting signal is read by output stage 103 connected to track CL. Transistor RS being bidirectional, it also enables to reset photodiode PS to a determined potential before the beginning of a new integration period.

As an example, a plurality of elementary cells 101 may be connected to a same output track CL and share a same output stage 103 of the sensor. Cells 101 are for example arranged in an array of rows and columns, the cells of a same column being connected to a same output track CL and to a same output stage 103, and the cells of different columns being connected to different output tracks CL and to different output stages 103. As an example, cells 101 are simultaneously controllable row by row, that is, the cells 101 of a same row have their nodes $VG_{RS}$ connected to a same control track and the cells 101 of different rows have their nodes $VG_{RS}$ connected to different control tracks.

Figure 2:
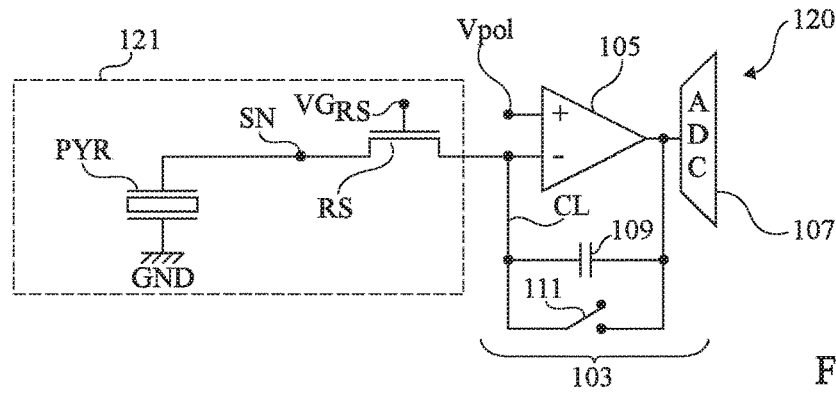
FIG. 2 is a partial electric diagram illustrating an example of a thermal TFT print sensor.

FIG. 2 is an electric diagram illustrating an example of a thermal TFT print sensor 120. Sensor 120 of FIG. 2 comprises elements common with sensor 100 of FIG. 1. These elements will not be described again. Sensor 120 differs from sensor 100 mainly in that, in sensor 120, elementary thermal-type acquisition cells 121 replace the elementary optical acquisition cells 101 of sensor 100. Elementary cells 121 of the sensor of FIG. 2 differ from elementary cells 101 of the sensor of FIG. 1 in that, in each cell 121, a pyroelectric conversion element PYR, coupling sense node SN of the cell to node GND, replaces photodetector PS of cells 101. Pyroelectric conversion element PYR typically comprises a layer of a pyroelectric material such as aluminum nitride (AlN), zinc oxide (ZnO), a polymer such as polyvinylidene fluoride (PVDF), having a pyroelectric coefficient in the order of 40 $\mu C/m^2/K$, a PZT-type ceramic material (lead zirconium titanium), having a pyroelectric coefficient in the order of 350 $\mu C/m^2/K$, or a TGS- or $LiTaO_3$-type crystalline element (Triglycine sulfate), arranged between two conductive layers respectively connected to node SN and to node GND.

Sensor 120 further differs from sensor 100 of FIG. 1 in that it comprises no backlighting light source, but comprises a heat source, not shown. As an example, the heat source may comprise a network of resistors regularly distributed across the sensor surface. As an example, the heat source comprises one resistor per elementary cell, the resistor being arranged in the vicinity of the pyroelectric element of the cell. The resistors of the heat source are preferably arranged on the same side of the support substrate as cells 101, that is, on the upper surface side of the substrate.

Sensor 120 operates as follows. The user has placed one (or a plurality of) finger(s) on or above the upper surface of the sensor (on the side of cells 121). The heat source of the sensor is then turned on, and heats pyroelectric conversion elements PYR, which accordingly generate electric charges on the sense nodes SN of the corresponding cells 121. The quantity of heat received by each pyroelectric conversion element PYR when the heat source is turned on is greater when the corresponding cell is topped with a skin valley than when it is topped by a ridge. Indeed, when the cell is topped with a ridge, the skin absorbs a more significant part of the heat emitted by the source than when the cell is topped with a valley. Thus, when a cell 121 is topped with a skin valley, the quantity of electric charges generated on its sense node SN is greater than when the cell is topped with a ridge. At the end of an integration period during which the cell readout transistor RS is kept off, the charges accumulated on node SN are transferred onto output track CL of the cell via transistor RS, and the resulting signal is read by output stage 103 connected to track CL. Transistor RS being bidirectional, it also enables to reset node SN before the beginning of a new integration period.

Preferably, during an acquisition, the heat source is controlled to generate a heat pulse, and the cells are read from some time after the beginning of the pulse, and/or little after the end of this pulse, to do away with thermalization phenomena causing, over time, the uniformization of the charge levels accumulated on the sense nodes SN of the different cells.

As in the example of FIG. 1, a plurality of elementary cells 121 may be connected to a same output track CL and share a same output stage 103 of the sensor. Cells 121 are for example arranged in an array of rows and columns, the cells of a same column being connected to a same output track CL and to a same output stage 103, and the cells of different columns being connected to different output tracks CL and to different output stages 103. As an example, cells 121 are simultaneously controllable row by row. Preferably, the heat source is then controllable to heat cells 121 row by row. This enables to perform a row-by-row scanning of the sensor by synchronizing the turning on of the heat source with the cell reading, and thus to minimize the effects of thermalization on the acquired image. In this case, the heat source may be formed of conductive tracks extending along the sensor rows, for example, metal tracks (for example, made of molybdenum or of aluminum), tracks made of a metal oxide, possibly transparent (for example, made of indium tin oxide), polysilicon tracks, or tracks made of a conductive polymer.

In sensors 100 and 120 of FIGS. 1 and 2, elementary acquisition cells 101 and 121 are charge readout cells, that is, the reading from a cell comprises transferring, onto output track CL of the cell (via readout transistor RS of the cell), charges accumulated on sense node SN of the cell. An advantage of charge readout acquisition cells is that they are particularly simple and/or compact (a single transistor per cell in the examples of FIGS. 1 and 2). Such cells are particularly adapted to TFT technologies, for example, based on amorphous silicon or indium gallium zinc oxide, where the transistors are relatively bulky. As a non-limiting illustration, in print sensors of the type described in the present application, the pixel pitch may typically be in the range from 20 to 50 µm, which limits the number of transistors that each cell may comprise.

Figure 3:
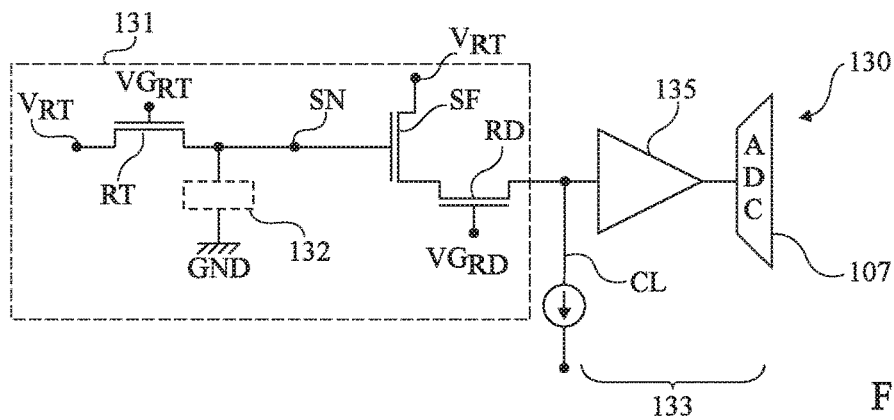
FIG. 3 is a partial electric diagram illustrating another example of an optical or thermal TFT print sensor.

FIG. 3 is an electric diagram illustrating another example of an optical or thermal TFT print sensor 130. Sensor 130 of FIG. 3 comprises elements common with sensors 100 and 120 of FIGS. 1 and 2. These elements will not be described again. Sensor 130 of FIG. 3 differs from sensors 100 or 120 of FIGS. 1 and 2 essentially in that, in sensor 130, elementary voltage readout acquisition cells 131 replace charge readout cells 101 or 121 of sensors 100 or 120. Sensor 130 further differs from sensors 100 and 120 in that, in sensor 130, one or a plurality of output stages 133 replace the output stage(s) 103 of sensors 100 or 120. In sensor 130, each elementary acquisition cell 131 comprises a photoelectric or pyroelectric conversion element 132 connected between a capacitive sense node SN of the cell and a node of application of a reference potential GND of the cell. As an example, conversion element 132 is an optical conversion element PS of the type described in relation with FIG. 1 or a thermal conversion element PYR of the type described in relation with FIG. 2. Each cell 131 further comprises a reset transistor RT coupling its sense node SN to a node of application of a reset potential $V_{RT}$, for example, a potential which is positive relative to GND. Each cell 131 further comprises a transistor SF assembled as a follower source, having its gate connected to node SN, and a readout transistor RD coupling the source of transistor SF to output track CL of the cell. The drain of transistor SF is coupled to a node of application of a reference potential, for example, potential $V_{RT}$ or another potential. The control gate of transistor RT is connected to a node $VG_{RT}$ of application of a control potential of this transistor, and the gate of transistor RD is connected to a node $VG_{RD}$ of application of a control potential of this transistor.

Output track CL of cell 131 is connected to an output stage 133 of the sensor. In this example, output stage 133 comprises an amplifier 135 having an input coupled to track CL and having its output coupled to an analog-to-digital converter 107 (ADC). Amplifier 135 is optional, and may in particular be omitted if the potential level of track CL is compatible with the input of analog-to-digital converter 107.

Sensor 130 further comprises an illumination light source (not shown) if elements 132 are optical acquisition elements, or a heat source (not shown) if elements 132 are pyroelectric acquisition elements.

The operation of an elementary cell 131 of sensor 130 during a print acquisition phase will now be described. Conversion element 132 of the cell is first reset via cell transistor RT. Transistor RT is then turned off and, during an integration period, photogenerated charges or charges generated by pyroelectric effect accumulate on sense node SN of the cell. At the end of the integration, the potential of sense node SN is transferred onto output track CL of the cell via transistors SF and RD. To achieve this, transistor RD of the cell is turned on. The potential of output track CL is then read by the output stage 133 associated with output track CL.

An advantage of voltage readout acquisition cells is that they provide a better signal-to-noise ratio than charge readout cells of the type described in relation with FIGS. 1 and 2.

Figure 4:
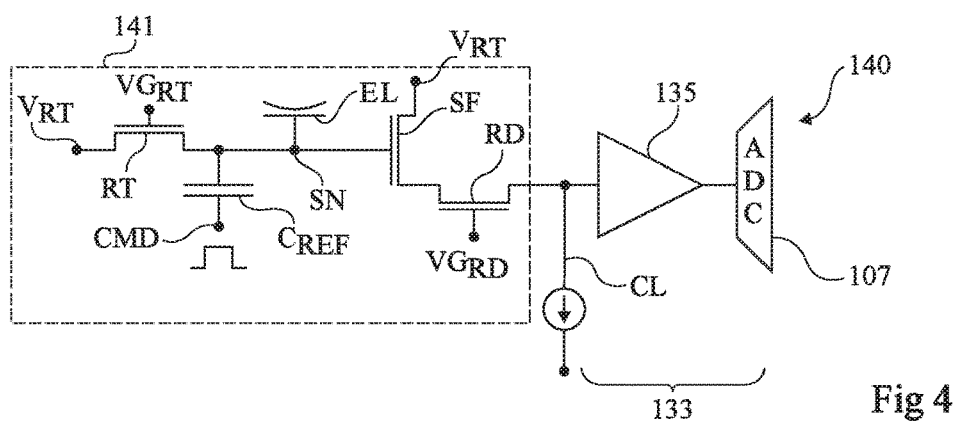
FIG. 4 is a partial electric diagram illustrating an example of a capacitive TFT print sensor.

FIG. 4 is an electric diagram illustrating an example of a capacitive TFT print sensor 140. In the shown example, sensor 140 is a voltage readout sensor. Sensor 140 comprises elements common with sensor 130 of FIG. 3. These elements will not be described again hereafter. Sensor 140 differs from sensor 130 of FIG. 3 essentially in that, in sensor 140, capacitive-type elementary acquisition cells 141 replace the optical or thermal acquisition cells 131 of sensor 130. In this example, sensor 140 comprises no illumination light source and no heat source. Each cell 141 comprises the same elements as a cell 131 of the sensor of FIG. 3, except for optical or pyroelectric conversion element 132. Each cell 141 further comprises a reference capacitor $C_{REF}$, connected between sense node SN of the cell and a node CMD of application of a control signal. Each cell 141 further comprises a conductive electrode EL connected to node SN, electrode EL being coated with a dielectric layer and being intended to form a capacitance with the user's finger skin. Electrode EL is preferably placed in the vicinity of the upper surface of the sensor, so that the dielectric thickness between the upper surface of the sensor (intended to receive the user's finger) and electrode EL does not exceed a few microns, for example, 10 μm.

Sensor 140 operates as follows: The user places one (or a plurality of) finger(s) on or above the upper surface of the sensor (on the side of electrodes EL). On acquisition of an image point of the print by a cell 141, sense node SN of the cell is first reset via transistor RT of the cell. Transistor RT is then turned off, and then a control signal, for example, a square or stepped voltage, is applied to control node CMD of the cell. Reference capacitance $C_{REF}$ and the capacitance formed between electrode EL and the finger skin form a capacitive dividing bridge. A potential depending on the capacitance formed between electrode EL and the skin then settles on sense node SN of the cell. The value of this potential is different according to whether electrode EL is topped with a ridge or with a valley of the user's skin. The potential of node SN is transferred onto output track CL of the cell via transistors SF and RD. To achieve this, transistor RD of the cell is turned on. The potential of output track CL is then read by the output stage 133 associated with output track CL. The step applied to node CMD can then be taken back to its initial value.

According to an aspect of described embodiments, a print sensor formed in TFT technology is provided, the sensor comprising, on a transparent insulating support substrate, for example, made of glass, a plurality of elementary acquisition cells, each cell comprising a photodetector, a pyroelectric conversion element, and at least one TFT. In other words, it is provided to combine, in each elementary cell, an optical acquisition element and a thermal acquisition element, so that the sensor supplies, during the acquisition of a fingerprint or a palmprint, an optical image and a thermal image of the print.

An advantage of such a sensor is that the two images are acquired by means of acquisition elements based on phenomena which have, offhand, no physical relation. Indeed, the photodetector generates electric charges when it receives photons, and the pyroelectric element generates electric charges when its temperature varies. This enables to solve, to a certain extent, the difficulties encountered in the acquisition of so-called "difficult" fingerprints, that is, certain types of fingers on which usual sensors do not succeed in satisfactorily discriminating skin ridges from skin valleys. The inventors have indeed observed that, generally, a print which is difficult to acquire in the optical field is easier to acquire in the thermal field and, conversely, a print which is difficult to acquire in the thermal field is easier to acquire in the optical field.

The fact of integrating the photodetector and the pyroelectric conversion element in a same elementary cell enables to share cell control TFTs between the photodetector and the pyroelectric conversion element, and thus to limit the bulk, the complexity, and the cost of the sensor. Preferably, as will be detailed hereafter in relation with FIGS. 6, 7, 8, 9, and 10, in each elementary cell, a same TFT of the cell is connected both to the photodetector and to the pyroelectric conversion element, which enables to limit the bulk. More particularly, in the embodiments of FIGS. 6, 7, and 8, in each elementary cell, the photoelectric and pyroelectric conversion elements are connected in parallel, which enables to obtain particularly simple and compact elementary cells.

Figure 5:
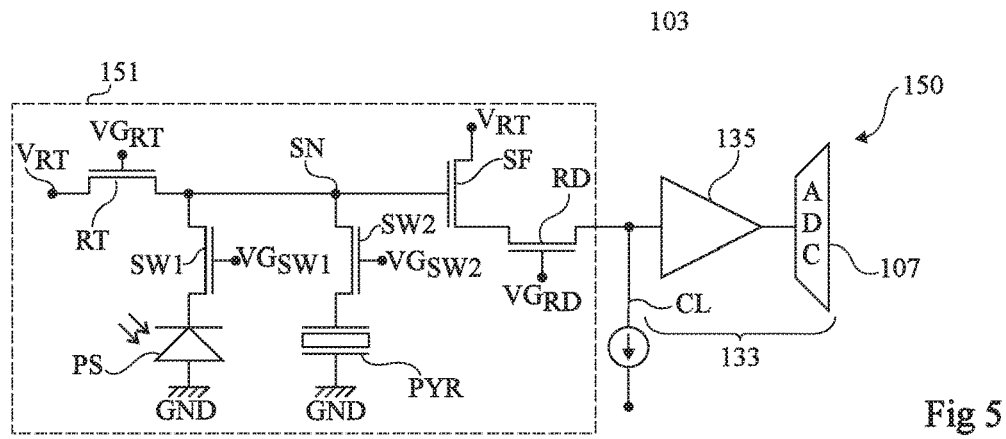
FIG. 5 is a partial electric diagram illustrating another embodiment of a TFT print sensor.

FIG. 5 is an example of an optical and thermal TFT print sensor 150. Sensor 150 of FIG. 5 is a voltage readout sensor. Sensor 150 of FIG. 5 comprises elements common with sensor 130 of FIG. 3. These elements will not be described again. Sensor 150 of FIG. 5 differs from sensor 130 of FIG. 3 essentially in that, in sensor 150, elementary voltage readout acquisition cells 151, both optical and thermal, replace optical or thermal cells 131 of sensor 130. In sensor 150, each elementary acquisition cell 151 comprises the same elements as an elementary acquisition cell 131 of sensor 130, except for conversion element 132. Each cell 151 further comprises a photodetector PS, for example, of the type described in relation with FIG. 1, in series with a selection transistor SW1 between the capacitive sense node SN of the cell and the reference node GND of the cell In the shown example, photodetector PS is a photodiode having its anode connected to node GND and having its cathode coupled to node SN via transistor SW1. Each cell 151 further comprises a pyroelectric conversion element PYR, for example, of the type described in relation with FIG. 2, in series with a selection transistor SW2 between sense node SN of the cell and node GND. In the shown example, pyroelectric element PYR has a first electrode connected to node GND and a second electrode coupled to node SN via a transistor SW2. The gate of transistor SW1 is coupled to a node $VG_{SW1}$ of application of a signal for controlling this transistor, and the gate of transistor SW2 is coupled to a node $VG_{SW2}$ of application of a signal for controlling this transistor.

Sensor 150 further comprises an illumination light source (not shown) intended for the implementation of an optical acquisition of an image, and a heat source (not shown), different from the light source, intended for the implementation of a thermal acquisition of an image.

As in the previous examples, cells 151 may be arranged in an array of rows and columns, the cells of a same row being simultaneously controlled and the cells of different rows being successively controlled. Further, as in the example of FIG. 2, the heat source may be controllable to heat cells 151 row by row.

In the example of FIG. 5, transistors SW1 and SW2 enable to isolate photodetector PS and/or pyroelectric element PYR from sense node SN. Two images, respectively optical and thermal, can thus be successively acquired by the sensor. During the acquisition of the optical image, transistors SW1 are in the conductive state and transistors SW2 are non-conductive. During the acquisition of the thermal image, transistors SW2 are in the conductive state and transistors SW1 are in the non-conductive state. For the rest, the sensor may be controlled identically or similarly to what has been described in relation with FIG. 3. In this example, reset transistor RT and transistors SF and RD of the readout stage are shared by the two conversion elements PS and PYR. It should be noted that the example of FIG. 5 may be adapted to form a charge readout optical and thermal sensor, by replacing, in the sensor of FIG. 1, photodetector PS with the assembly formed, in the example of FIG. 5, of transistors SW1 and SW2, photodetector PS, and pyroelectric element PYR.

However, a disadvantage of sensor 150 is the additional cost and the bulk due to the presence, in each elementary acquisition cell, of the two selection transistors SW1 and SW2.

Figure 6:
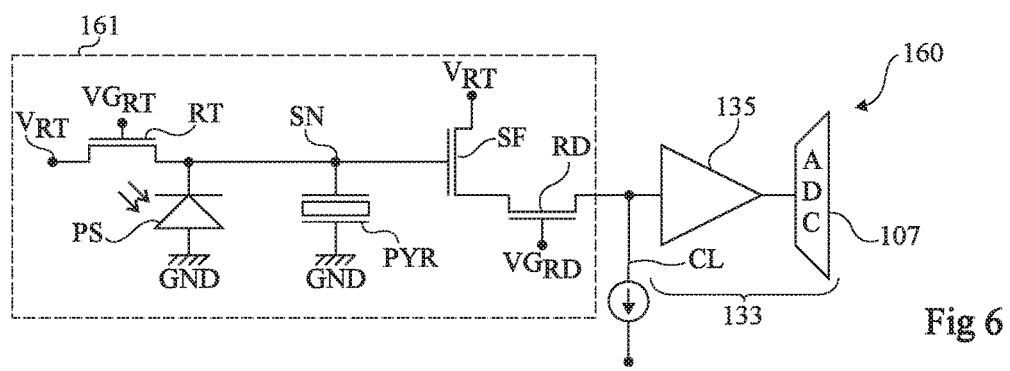
FIG. 6 is a partial electric diagram illustrating a first embodiment of a TFT print sensor.

FIG. 6 is an electric diagram illustrating an example of an optical and thermal TFT print sensor 160 according to a first embodiment. Sensor 160 of FIG. 6 is a voltage readout sensor. The sensor comprises elements common with sensor 150 of FIG. 5. These elements will not be described again. Sensor 160 of FIG. 6 differs from sensor 150 of FIG. 5 essentially in that, in sensor 160, elementary acquisition cells 161, both optical and thermal, replace optical or thermal cells 151 of sensor 150. Cells 161 of sensor 160 differ from cells 151 of sensor 150 in that they do not comprise transistors SW1 and SW2 of cells 151. More particularly, in each cell 161, photodetector PS (and more particularly the cathode node of photodiode PS in the shown example) is connected to node SN, and pyroelectric element PYR is connected to node SN. In other words, photodetector PS and pyroelectric element PYR are connected in parallel between node SN and node GND. Thus, in this example, photodetector PS and pyroelectric element PYR are directly connected to node SN, and accordingly to transistors RT and SF of the cell.

Sensor 160 further comprises an illumination light source (not shown) intended to implement an optical acquisition of an image, and a heat source (not shown), intended to implement a thermal acquisition of an image. The light source and the heat source are for example controllable, via a control circuit, not shown, in order to, during a print acquisition phase, be alternately turned on and then turned off. Thus, during a phase of acquisition of a thermal image of the print, the light source may be turned off, and the heat source may be turned on. As a result, only pyroelectric element PYR is capable of generating electric charges representative of the pattern of the print to be acquired. During a phase of acquisition of an optical image of the print, the light source may be turned on, and the heat source may be turned off. As a result, only photodetector PS is capable of generating electric charges representative of the pattern of the print to be acquired. For the rest, sensor 160 may be controlled identically or similarly to what has been described in relation with FIG. 3.

As a non-limiting example, during the acquisition of a print, the following control sequence may be implemented:

resetting of sense node SN by setting transistor RT to the conductive state, and then to the non-conductive state;

turning on of the heat source after the turning off of transistor RT, and holding the light source in the off state;

turning off of the heat source and reading of the potential of node SN to supply a thermal image of the print;

resetting of sense node SN by setting transistor RT to the conductive state, and then to the non-conductive state;

turning on of the light source after the turning off of transistor RT, and holding the heat source in the off state; and reading the potential of node SN to supply an optical image of the print (after an integration period).

It should be noted that the order of acquisition of the optical and thermal images may be inverted.

It should further be noted that the reset potential levels applied for the optical acquisition and for the thermal acquisition are not necessarily the same. Different reset levels may in particular be provided to balance the levels of the output signals, and optimize the use of an analog-to-digital converter.

It should further be noted that the readings of the optical signal and of the thermal signal may be readings of correlated double sampling type (generally designated with acronym CDS), where the output value is equal to the difference between a useful signal level and a reset level read from track CL. Thus, in the above-mentioned sequence, as well as in the control sequences described hereafter, a reading of the reset level may be performed, via track CL, after each resetting of sense node SN.

As a variation, during the acquisition of the thermal image, the heat source may be turned on before the end of the sense node resetting phase (that is, before turning off reset transistor RT), to do away with possible parasitic noise due to transient effects of current draw by the heat source. Further, during the acquisition of the optical image, the light source may be turned on before the end of the sense node resetting phase, to do away with possible parasitic noise due to transient effects of current draw by the light source.

Further, advantage may be taken of the fact that, generally, the acquisition of a thermal image point by pyroelectric element PYR is much faster than the acquisition of an optical image point by photodetector PS. As a non-limiting illustration, during the acquisition of a thermal image, the reading from node SN of a potential representative of the print pattern is performed from 10 to 500 μs after the turning on of the heat source (particularly to do away with a possible contrast alteration due to the thermalization) and, during an acquisition of an optical image, the photodetector integration time is in the range from 10 to 50 ms. As a variation, it may be provided to keep the backlighting light source on during the thermal acquisition, and to neglect the photo-generated charges generated by photodetector PS during the thermal acquisition. This enables to simplify the control of the light source. Further, the thermal acquisition may be performed during the optical integration period, which enables to decrease the total time necessary for the acquisition of the optical and thermal images. At the end of the optical integration period, the charges generated on sense node SN by pyroelectric element PYR may indeed be neglected, since the temperature at the beginning and at the end of the optical integration period is practically the same. In this case, the thermal acquisition is preferably carried out at the beginning of the optical integration period, for example, in the first half of the optical integration period, or at least 500 μs before the end of the optical integration period, to ensure that the charges generated by the pyroelectric element on node SN during the thermal acquisition have time to cancel by thermalization effect before the end of the optical integration period.

As a non-limiting example, during the acquisition of a print, the following control sequence may be implemented:

turning on of the backlighting light source (the light source may be permanently on);

resetting of sense node SN by setting transistor RT to the conductive state;

turning on of the heat source, and setting of transistor RT to the non-conductive state;

turning off of the heat source (typically from 20 to 50 µs after its turning on) and reading of the potential of node SN in order to provide a thermal image of the print (the charges photogenerated by element PS may be neglected);

carrying on of the optical integration with no resetting of sense node SN (meanwhile, the other cells of the array may be read to supply a thermal image); and reading of the potential of node SN, typically from 10 to 50 ms after the resetting of the cell, in order to supply an optical image of the print (the thermal signal may then be neglected since the cell temperature has substantially returned to its initial state).

An advantage of sensor 160 of FIG. 6 is the small number of transistors per elementary cell 161 with respect to the sensor of FIG. 5.

Preferably, but without this being a limitation, the dimensions (surface areas and/or thicknesses) of photodetector PS and of pyroelectric element PYR, the power of the backlighting light source, the photodetector integration time, and the power of the heat source, are selected so that the voltage levels generated on node SN during an optical acquisition and during a thermal acquisition are of the same order of magnitude, or at least remain in both cases within a voltage level range acceptable for the output stage. As a non-limiting example, the above parameters are selected so that, for a same type of skin structure (ridge or valley) above an elementary cell, the voltage level generated on node SN during an optical acquisition is in the range from 0.5 to 2 times the voltage level generated on node SN during a thermal acquisition.

Figure 7:
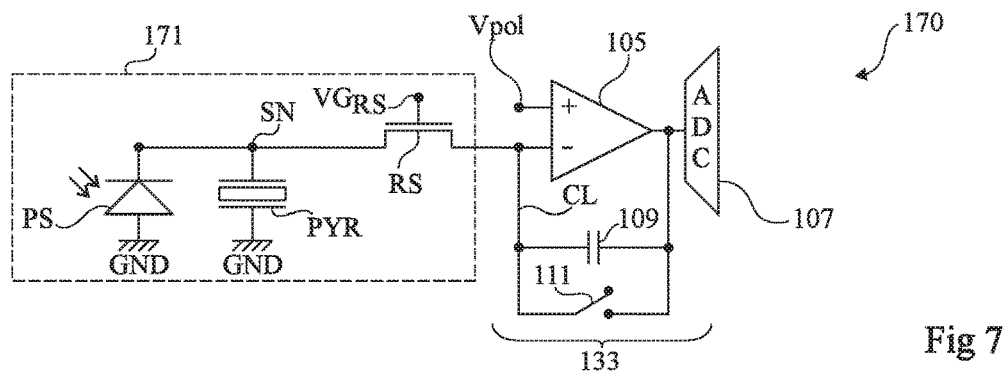
FIG. 7 is an electric diagram illustrating an alternative embodiment of the sensor of FIG. 6.

FIG. 7 is an electric diagram illustrating another example of an optical and thermal TFT print sensor 170 according to the first embodiment. Sensor 170 of FIG. 7 is a charge readout sensor. The sensor comprises elements common with sensors 100 and 120 of FIGS. 1 and 2. These elements will not be described again. Sensor 170 of FIG. 7 differs from sensors 100 and 120 of FIGS. 1 and 2 essentially in that, in sensor 170, elementary acquisition cells 171, both optical and thermal, replace optical cells 101 or thermal cells 121 of sensors 100 and 120. Cells 171 of sensor 170 differ from cells 101 or 121 of sensors 100 and 120 in that they comprise a photodetector PS and a pyroelectric element PYR connected in parallel between nodes SN and GND of the cell. Thus, in this example, readout transistor RS of the cell is directly connected both to photodetector PS and to pyroelectric element PYR. Transistor RS is shared by photodetector PS and pyroelectric element PYR.

Sensor 170 further comprises, as in the example of FIG. 6, an illumination light source (not shown) intended to implement an optical acquisition of an image, and a heat source (not shown), intended to implement a thermal acquisition of an image. The light source and the heat source are for example controllable via a control circuit, not shown, identically or similarly to what has been described in relation with FIG. 6.

The operation of sensor 170 is identical or similar to what has been described in relation with FIG. 6, with the difference that, in sensor 170, the elementary acquisition cells are charge readout cells. In particular, the resettings of the cells are performed via their readout transistors RS.

Similarly to what has been described in the example of FIG. 6, the dimensions (surface areas and/or thicknesses) of photodetector PS and of pyroelectric element PYR, the power of the backlighting light source, the photodetector integration time, and the power of the heat source, are preferably selected so that the quantities of charges generated on node SN during an optical acquisition and during a thermal acquisition are of the same order of magnitude.

Figure 8:
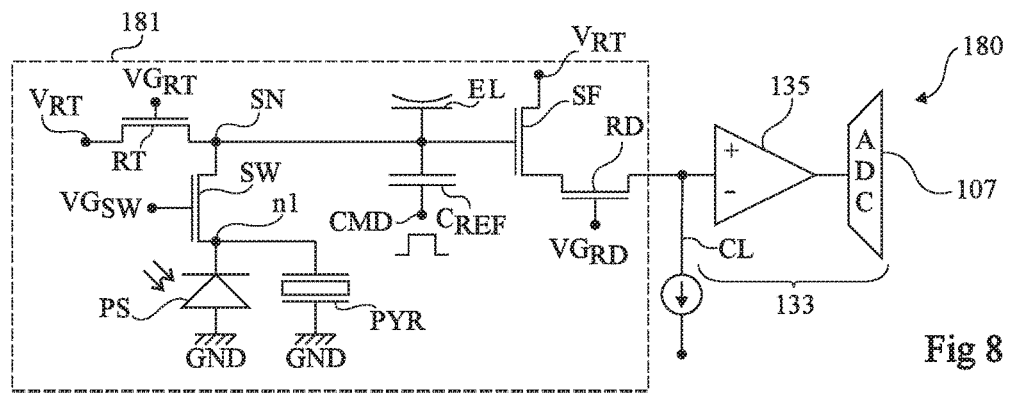
FIG. 8 is an electric diagram illustrating another alternative embodiment of the sensor of FIG. 6.

FIG. 8 is an electric diagram illustrating another example of an optical and thermal TFT print sensor 180 according to the first embodiment, the sensor further comprising capacitive-type acquisition means. Sensor 180 of FIG. 8 is a voltage readout sensor. The sensor comprises elements common with sensor 160 of FIG. 6. These elements will not be described again. Sensor 180 of FIG. 8 differs from sensor 160 of FIG. 6 essentially in that, in sensor 180, elementary acquisition cells 181 replace cells 161 of sensor 160. Cells 181 of the sensor differ from cells 161 of sensor 180 in that they comprise capacitive-type print acquisition means, for example, of the type described in relation with FIG. 4. More particularly, in the shown example, each cell 181 comprises a selection transistor SW coupling sense node SN of the cell to photodetector PS and to pyroelectric element PYR. More particularly, in each cell 181, photodetector PS and pyroelectric element PYR are connected in parallel between node GND and an intermediate node n1, and selection transistor SW is connected between node n1 and node SN. In the shown example, photodetector PS is a photodiode having its anode connected to node GND and having its cathode connected to node n1. The gate of selection transistor SW is connected to a node $VG_{SW}$ of application of a signal for controlling the transistor. Further, in the shown example, each cell 181 comprises a reference capacitor $C_{REF}$ connected between sensor node SN of the cell and a node CMD of application of a control signal, and a conductive electrode EL connected to node SN, electrode EL being coated with a dielectric layer and being intended to form a capacitance with the skin of a user's finger. As a variation, transistor RT may be connected between nodes $V_{RT}$ and n1.

In the example of FIG. 8, transistor SW enables to isolate the capacitive acquisition stage from the optical and pyroelectric acquisition stage. This particularly enables, during the implementation of a capacitive acquisition, for the capacitances of photodetector PS and of pyroelectric element PYR not to contribute to increasing the capacitance of sense node SN, which would make the acquisition of a capacitive-type print signal on node SN difficult.

In the example of FIG. 8, three images of a same print, respectively optical, thermal, and capacitive, may be acquired by the sensor. Reset transistor RT and transistors SF and RD of the readout stage, are shared by the three capacitive, photoelectric, and pyroelectric conversion elements. During the acquisition of the capacitive image, transistors SW of cells 181 may be set to the non-conductive state, and the cells may be controlled similarly or identically to what has been described in relation with FIG. 4. During the acquisition of the thermal and optical images, the transistors SW of cells 181 may be set to the conductive state, and the cells may be controlled similarly or identically to what has been described in relation with FIG. 6. It should be noted that the capacitance of elements PYR and PS is generally relatively large as compared with the capacitance of node SN (and particularly capacitance $C_{REF}$). Thus, the thermal and optical signals are not significantly altered by the capacitance of node SN when transistor SW is in the conductive state. As a variation, the light integration by photodetector PS may be partly or totally carried out during the capacitive reading, which enables to decrease the total print acquisition time. As described in relation with FIG. 6, the backlighting source may further be maintained for the entire print acquisition time, assuming that the thermal information readout time is negligible as compared with the photodetector integration time.

As a non-limiting example, during the acquisition of a print, the following control sequence may be implemented:

resetting of sense node SN by setting transistor RT to the conductive state and resetting of node n1 by setting transistor SW to the conductive state;

turning off of selection transistor SW to isolate the optical and thermal acquisition stage from the rest of the cell (the turning off of transistor SW marks the beginning of the period of light integration by photodetector PS);

turning off of reset transistor RT to isolate sense node SN from node $V_{RT}$, and reading of the reference value for the capacitive reading;

capacitive reading of the print;

turning on of the heat source before the end of the capacitive reading;

at the end of the capacitive reading, optional resetting of sense node SN by turning transistor RT on and then back off;

turning on of selection transistor SW and reading of the reference value for the thermal and optical readout operations;

turning off of the light source and reading of the potential of node SN to supply a thermal image of the print (the optical signal may be neglected since the durations of the capacitive signal and thermal acquisitions are relatively short as compared with the integration time of the optical acquisition);

carrying on of the optical integration with no resetting of sense node SN (meanwhile, the other cells of the array may be read from); and reading of the potential of node SN at the end of the photodetector integration period, to supply an optical image (the thermal signal can then be neglected since the cell temperature has substantially returned to its initial state).

Figure 9:
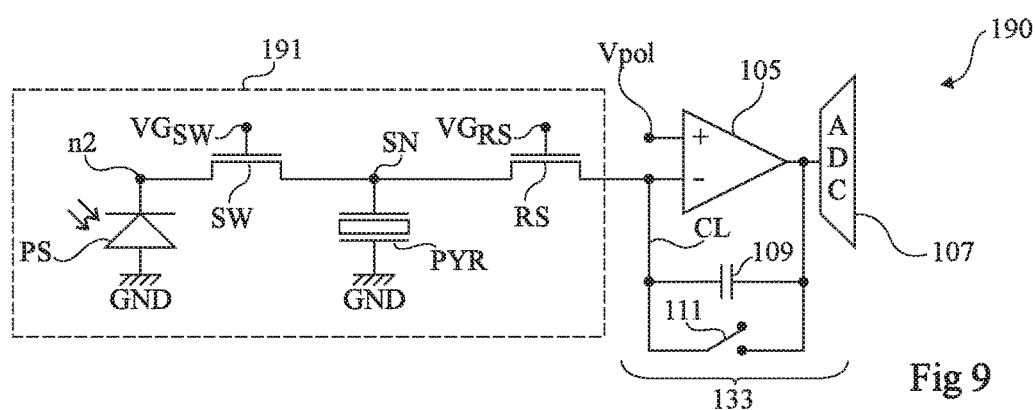
FIG. 9 is a partial electric diagram illustrating a second embodiment of a TFT print sensor.

FIG. 9 is an electric diagram illustrating an example of an optical and thermal TFT print sensor 190 according to a second embodiment. Sensor 190 of FIG. 9 is a charge readout sensor. The sensor comprises elements common with sensor 170 of FIG. 7. These elements will not be described again. Sensor 190 of FIG. 9 differs from sensor 170 of FIG. 7 essentially in that, in sensor 190, elementary acquisition cells 191 replace cells 171 of sensor 170. Cells 191 of sensor 190 differ from cells 171 of sensor 170 in that, in cells 191, photodetector PS is not directly connected between nodes GND and SN, but is connected between node GND and an intermediate node n2, node n2 being coupled to node SN by a selection transistor SW. Pyroelectric element PYR is directly connected to node SN. More particularly, in this example, photodetector PS is a photodiode having its anode connected to node GND and having its cathode connected to node n2. Thus, selection transistor SW is connected both to photodetector PS and to pyroelectric element PYR. Readout transistor RS of the cell is shared by photodetector PS and pyroelectric element PYR.

In sensor 190, transistors SW enable, in each elementary acquisition cell, to isolate photodetector PS from the rest of the cell.

An advantage is that this provides additional control possibilities with respect to sensor 170 of FIG. 7, while limiting the cost and the bulk with respect to a sensor with two selection transistors SW1 and SW2 per cell, such as described in relation with FIG. 5. Further, this provides more flexibility in terms of sizing of optical and thermal conversion elements PS and PYR than in a sensor of the type described in relation with FIG. 7.

As a non-limiting example, during the acquisition of a print, the following control sequence may be implemented:

resetting of sense node SN and of intermediate node n2 by setting transistors RS and SW to the conductive state;

turning off of selection transistor SW to isolate the photodetector from node SN, and turning off of transistor RS to isolate node SN from output track CL;

turning on of the heat source and of the illumination source (it should be noted that the illumination source may in practice be permanently on, photodetector PS being isolated from the pyroelectric element);

turning off the heat source and reading of the potential of node SN to provide a thermal image of the print;

carrying on of the optical integration (meanwhile, the other cells of the array may be read from to provide the thermal image); and turning on of transistor SW and reading of the potential of node SN at the end of the photodetector integration period, to provide an optical image.

Figure 10:
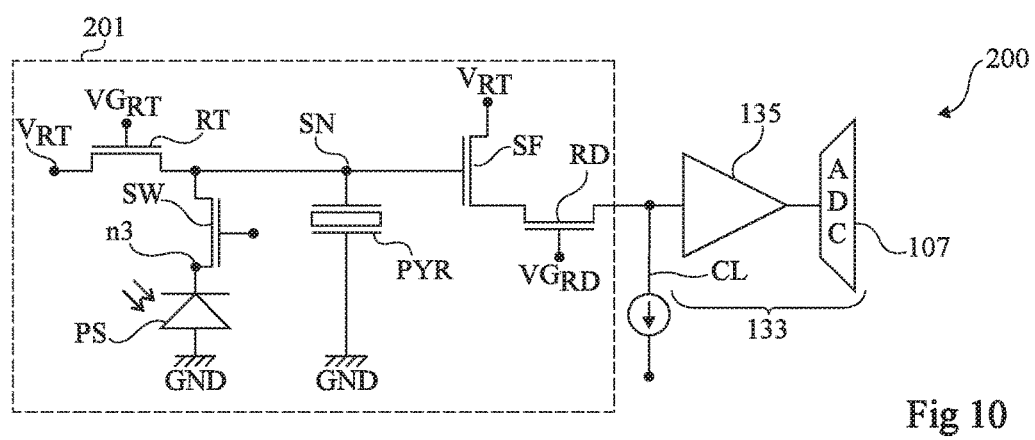
FIG. 10 is an electric diagram illustrating an alternative embodiment of the sensor of FIG. 9.

FIG. 10 is an electric diagram illustrating another example of an optical and thermal TFT print sensor 200 according to the second embodiment. Sensor 200 of FIG. 10 is a voltage readout sensor. The sensor comprises elements common with sensor 160 of FIG. 6. These elements will not be described again. Sensor 200 of FIG. 10 differs from sensor 160 of FIG. 6 essentially in that, in sensor 200, elementary acquisition cells 201 replace cells 161 of sensor 160. Cells 201 of sensor 200 differ from cells 161 of sensor 160 in that, in cells 201, photodetector PS is not directly connected between nodes GND and SN, but is connected between node GND and an intermediate node n3, node n3 being coupled to node SN by a selection transistor SW. Pyroelectric element PYR is directly connected to node SN. More particularly, in this example, photodetector PS is a photodiode having its anode connected to node GND and having its cathode connected to node n3. Thus, selection transistor SW is connected both to photodetector PS and to pyroelectric element PYR. Transistors RT, SF, and RD of the cell are shared by photodetector PS and pyroelectric element PYR.

In sensor 200, transistors SW enable, in each elementary acquisition cell, to isolate photodetector PS from the rest of the cell, which provides additional control possibilities with respect to sensor 160 of FIG. 6, while limiting the cost and the bulk with respect to a sensor with two selection transistors SW1 and SW2 per cell, such as described in relation with FIG. 5. Further, this provides more flexibility in terms of sizing of optical and thermal conversion elements PS and PYR than in a sensor of the type described in relation with FIG. 6.

As a non-limiting example, during the acquisition of a print, the following control sequence may be implemented:

turning on of the illumination light source (in this example, the light source may be permanently on);

resetting of sense node SN by setting transistor RT to the conductive state, and then turning off of transistor RT;

turning on of transistor SW the charges photogenerated by photodetector PS since its previous resetting are then distributed all over the capacitance of sense node SN;

reading of the potential of node SN at the end of the photodetector integration period, to provide an optical image;

resetting of nodes n3 and SN by setting transistors RT and SW to the conductive state;

turning off of transistor SW to isolate photodetector PS from node SN (which defines the beginning of a new integration period of photodetector PS);

turning off of reset transistor RT;

turning on of the heat source;

turning off the heat source and reading of the potential of node SN to supply a thermal image of the print.

As a variation, in the examples of FIGS. 9 and 10, photodetector PS and pyroelectric element PYR may be exchanged, that is, element PYR may be placed behind selection transistor SW between node n2 and n3 and node GND, photodetector PS being then directly connected to node SN. The choice may be performed according to the respective values of the capacitances of elements PYR and PS.

Specific embodiments have been described. Various alterations, modifications, and improvements will readily occur to those skilled in the art.

It should in particular be noted that, in an optical print sensor, the photodetector may generate, in addition to the useful signal representative of the pattern of the print to be acquired, noise due, in particular, to darkness currents and/or to the ambient light. To do away with such noise sources, it may be provided, in the above-mentioned embodiments, to perform a no-load reading, that is, with no finger placed on the sensor and without turning on the backlighting source or the light source, to acquire an image representative of the noise generated by photodetector PS (particularly due to darkness currents and to the parasitic ambient light). Once this image has been acquired, it may be subtracted to the final optical image and, if the photodetector is not isolated from the pyroelectric element, to the final thermal image.

Further, instead of performing two different readout operations, respectively thermal and optical, and attempting to distinguish the thermal signal from the optical signal, as has been described hereabove, it may be provided to read the sum of the photogenerated charges and of the charges generated by the pyroelectric element, without attempting to separate them, to acquire an image combining the optical signal and the thermal signal, which may result being useful to acquire certain difficult prints. As an example, in the embodiments of FIGS. 6, 7, and 8, it may be provided to first turn on the light source, and then, towards the end of the optical integration period, to turn on the heat source so that the pyroelectric element generates charges on node SN, and then to read from node SN a value representative of the sum of the optical signal and of the thermal signal.

Further, although examples of control methods where, during the acquisition of a print, an optical image and a thermal image are read, have been described hereabove, alternative embodiments where a plurality of optical images and/or a plurality of thermal images of the same print are read may be provided. As an example, if the optical integration period is several times greater than the time necessary to implement steps of thermal reading of all the sensor rows, it may be provided to successively scan the entire sensor a plurality of times to acquire a plurality of thermal images and then, at the last scanning of the sensor, to acquire the optical image.

Further, in the embodiments of FIGS. 9 and 10, selection transistor SW between photodetector PS and pyroelectric element PYR may advantageously be used to implement a "global shutter"-type readout sequence, that is, a sequence where, during the acquisition of an optical image, all the photodetectors PS of the sensor are simultaneously integrated. In each elementary acquisition cell, pyroelectric element PYR may then be used as a storage element to store the value acquired by the photodetector, while waiting for the reading thereof. Such an embodiment advantageously enables to use a short integration time as compared with the time taken to read the entire array, the light source being flashed synchronously with the acquisition. As a non-limiting example, during an acquisition of a print, the following control sequence may be implemented:

setting to the conductive state of the transistors SW of all the sensor cells;

resetting of all the sensor cells, and then setting of transistors SW to the conductive state;

turning on of the light source during the optical integration period of the sensor;

at the end of the integration period, turning on of selection transistors SW in all the sensor cells (charges photogenerated during the integration are then transferred onto node SN, in the capacitance formed by the pyroelectric element) and then turning off of selection transistors SW (the voltage across the photodiode may then keep on evolving independently from node SN);

reading, for example, row by row, from all the sensor cells, of the signal level stored on node SN to provide the optical image;

in each cell, after the reading of the optical signal, resetting of node SN by turning on transistor RT and by leaving transistor SW off;

turning on of the heat source;

turning off of the heat source and reading of the signal on node SN to provide a thermal image.

Further, the above-described embodiments may be combined with other fingerprint acquisition technologies, for example, ultrasound or electric field acquisition technologies, or technologies where a signal RF is applied through the user's skin.

Further, it will be within the abilities of those skilled in the art to adapt the described embodiments to form sensors implementing passive-type thermal image acquisitions, that is, sensors with no active heat source. In this case, the temperature variation used by pyroelectric conversion elements PYR is a variation which occurs when the user places his/her finger on the sensor, and/or removes it from the sensor. Such sensors may be of static type (the sensor surface area is at least equal to the surface area of the print to be acquired, and the finger does not move with respect to the sensor during the acquisition) or of scanning type (the sensor surface area is smaller than the surface area of the print to be acquired, and the finger passes in front of the sensor during the acquisition).

What is claimed is:

1. A fingerprint or palmprint sensor comprising:
   on a support substrate, a plurality of elementary acquisition cells realized in TFT technology, each cell comprising a photodetector and a pyroelectric conversion element coupled to a same capacitive sense node of the cell, and a readout circuit coupling the capacitive sense node of the cell to a conductive output track of the cell;
   an illumination light source; and
   a heat source distinct from the light source.

2. The sensor of claim 1, wherein the support substrate is transparent.

3. The sensor of claim 1, wherein the photodetector and the pyroelectric conversion element are connected in parallel.

4. The sensor of claim 1, comprising a circuit configured to control the acquisition of a thermal image and the acquisition of an optical image by the sensor cells, the circuit being configured to, during the entire optical image acquisition phase, turn on the light source and keep the heat source off and, during the entire thermal image acquisition phase, keep the light source off.

5. The sensor of claim 1, comprising a circuit configured to control the acquisition of a thermal image and the acquisition of an optical image by the sensor cells, the circuit being capable configured to implement the acquisition of the thermal image during part of an integration period of the optical image acquisition phase during which the light source is on.

6. The sensor of claim 1, wherein, in each cell, the photodetector and the pyroelectric conversion element are connected to the capacitive sense node of the cell.

7. The sensor of claim 1, wherein, in each cell, the photodetector and the pyroelectric conversion element are connected to an intermediate node of the cell, the intermediate node being coupled to the capacitive sense node of the cell by a selection transistor, and each cell further comprising:
   a reference capacitor connected between the capacitive sense node of the cell and a node of application of a control signal; and
   an electrode connected to the capacitive sense node of the cell, the electrode being coated with a dielectric layer and being intended to form a capacitance with a user's skin for a capacitive acquisition of a print image.

8. The sensor of claim 1, wherein the photodetector and the pyroelectric conversion element are connected to a same selection transistor enabling, in the off state, to isolate the photodetector from the pyroelectric element.

9. The sensor of claim 1, wherein the cells are arranged in an array of rows and columns, and wherein the heat source is controllable to heat the cells row by row.

10. The sensor of claim 1, wherein the cells are voltage readout cells, each cell comprising
    a reset transistor coupling the capacitive sense node of the cell to a node of application of a reset potential, and
    the readout circuit of each cell comprising a transistor assembled as a follower source, having its gate connected to the capacitive sense node of the cell, and having its source coupled to the output track of the cell via a readout transistor.

11. The sensor of claim 1, wherein the cells are charge readout cells, the readout circuit of each cell comprising
    a readout transistor coupling the capacitive sense node of the cell to the output track of the cell.

12. The sensor of claim 1, wherein the photodetector and the pyroelectric conversion element are connected to different selection transistors enabling to isolate the photodetector from the pyroelectric element.

\* \* \* \* \*

UNITED STATES PATENT AND TRADEMARK OFFICE
CERTIFICATE OF CORRECTION

PATENT NO. : 10,176,357 B2
APPLICATION NO. : 15/516402
DATED : January 8, 2019
INVENTOR(S) : Jean-François Mainguet, Joel Fourre and Josep Segura Puchades Page 1 of 1

It is certified that error appears in the above-identified patent and that said Letters Patent is hereby corrected as shown below:

On the Title Page

Item (73) Assignee, should read as follows:
Commissariat à l'Energie Atomique et aux Energies Alternatives
Paris, France
SAFRAN IDENTITY & SECURITY
Issy-Les-Moulineaux, France Signed and Sealed this
Sixteenth Day of April, 2019

Andrei Iancu
*Director of the United States Patent and Trademark Office*